(12) United States Patent
Schlichte

(10) Patent No.: US 6,303,102 B1
(45) Date of Patent: Oct. 16, 2001

(54) CUTANEOUSLY APPLIED BIODEGRADABLE TELL-TALE HAVING CONTROLLABLE CLEARING TIME

(76) Inventor: Kenneth Schlichte, 25014 K 42, Merrill, IA (US) 50138

( * ) Notice: Subject to any disclaimer, the term of this patent is extended or adjusted under 35 U.S.C. 154(b) by 0 days.

(21) Appl. No.: 09/657,191

(22) Filed: Sep. 7, 2000

(51) Int. Cl.⁷ .......................... A61K 49/00; A61K 10/00; C09D 51/14; C09D 11/00
(52) U.S. Cl. .................. 424/10.3; 424/9.321; 424/9.322; 424/10.1; 106/31.03; 106/31.13; 106/31.32; 106/31.64
(58) Field of Search .............................. 424/10.3, 9.321, 424/9.322, 9.6, 9.8, 10.1; 106/31.03, 31.13, 31.15, 31.32, 31.64

(56) References Cited

U.S. PATENT DOCUMENTS

| 3,416,530 | 12/1968 | Ness | 128/260 |
|---|---|---|---|
| 3,427,377 | 2/1969 | Bauer et al. | 424/7 |
| 4,152,412 | 5/1979 | Brewer | 424/7 |
| 4,572,831 | 2/1986 | Rosen | 424/7.1 |
| 6,013,122 | 1/2000 | Klitzmann et al. | 106/31.03 |

Primary Examiner—Zohreh Fay
Assistant Examiner—Brian-Yong Kwon
(74) Attorney, Agent, or Firm—McHale & Slavin

(57) ABSTRACT

The instant invention provides a biodegradable tell-tale composition which is applied cutaneously or subcutaneously to a human or animal subject for aiding in the determination of instillation or application of a medicament, vaccine or the like; and furthermore for providing, via the biodegradable functionality, a useful tool for measuring the period of time which has passed since the most recent inoculation.

24 Claims, No Drawings

CUTANEOUSLY APPLIED BIODEGRADABLE TELL-TALE HAVING CONTROLLABLE CLEARING TIME

FIELD OF THE INVENTION

The present invention relates to a marker that is useful in combination with all manners of vaccines, implants or treatment drugs, applied either topically or orally, in either animals or humans. The invention particularly relates to a combined medicament/marker having a controlled clearing time.

BACKGROUND OF THE INVENTION

In the treatment of both animals and humans, it is often useful to provide a means for marking the site where a medicament is injected, inserted or otherwise applied.

More specifically, when dealing with animals which are being raised for food, it is often required that the animals be inoculated with a variety of materials in order to insure that the food harvested therefrom is wholesome. Furthermore, certain medicaments, albeit useful during the animal's growth phase, are nevertheless prohibited at the time of harvest. Regulations prescribe time limits regarding the use of such medicaments to insure a sufficient time period for clearing via natural biodegradation prior to harvest.

Industry compliance with the stated guidelines is a particularly vexing problem, which the industry has been recalcitrant in monitoring. For example, although feedlot attendants may be supplied with the required immunization or medicament, they may be derelict in their responsibilities and fail to apply the material to the animal.

Alternatively, a particular material might need to be given a clearing time period, for example 30 days prior to harvest, thereby allowing a safe clearing time from the animal's flesh. If the feed lot attendant is tardy in making the application, or simply becomes confused about the dates or inoculates a group of animals in error, harmful concentrations of the prohibited materials may find their way into the food supply.

With regard to human applications, there are instances where certain inoculations or tests are initiated and follow-up must occur at a prescribed time interval. In other instances, medicaments are provided in the form insertable implants which reside within the body for extended periods. Furthermore, in a military or possibly a hospital or nursing care environment, it might be beneficial to include a visual confirmation that an individual has received an inoculation.

In all of the above noted circumstances, the inclusion of a marking ingredient or tell-tale which has a controlled biodegradability can act as either evidence of instillation or evidence that a particular period of time has elapsed subsequent to instillation or application of the medicament.

DESCRIPTION OF THE PRIOR ART

U.S. Pat. No. 6,013,122 discloses tattoo inks which can be designed to degrade after a predetermined time. However, there is no disclosure that these inks can be used as indicators to show how long ago a medication was administered.

U.S. Pat. No. 3,416,530 discloses a tablet-like body for insertion along the scleral radius. The tablet is designed to dispense medication to the eye at a predetermined and continuous rate, and utilizes a dye, such as methylene blue, to provide a visual indication that the tablet continues to dispense the medicament. The reference fails to provide a marking device capable of providing a residual marker subsequent to medicament dosage or one that remains visible for a predetermined clearing time.

U.S. Pat. No. 3,427,377 proposes a composition of penicillin and a dye of 2,4-disulfo-5-hydroxy-4', 4"-bis-(diethylamino)-triphenyl-carbinol calcium salt, for administration to the udders of dairy animals. This formulation indicates the presence of penicillin in milk as long as the antibiotic is excreted by the udders.

U.S. Pat. No. 4,572,831 teaches a combination of flourescamine or other furanones and a visible, fugitive dye or pigment. Said composition is useful in marking skin for radiological purposes without leaving visible markings on a patient for an extended period of time.

U.S. Pat. No. 4,152,412 to Brewer discusses an injectable marking vaccine carried on a physiologically acceptable colored particle (e.g., activated charcoal) so as to provide a clearly visible mark evidencing the administration of the desired vaccine.

What is lacking in the art is a cutaneously applied biodegradable tell-tale composition, which composition includes an effective amount of a marker formulation having a pigment or dye in combination with a suitable carrier therefore, and further containing a therapeutically effective amount of one or more medicaments having a controllable period of efficacy or clearing time, and including one or more of a variety of compatible medicaments, vaccines or combinations thereof; wherein instillation/application of the tell-tale marker formulation/medicament combination provide visual evidence for gauging both the application, per se, and time since application of said medicament.

SUMMARY OF THE INVENTION

The instant invention provides a biodegradable tell-tale composition which is applied cutaneously or subcutaneously to a human or animal subject for aiding in the determination of instillation of medicament and furthermore for providing, via the biodegradable functionality, a useful tool for measuring the period of time passed since the most recent inoculation.

It is envisioned that the tell-tale composition of the instant invention will have a plurality of utilities. For example:
1) the tell-tale composition can be given by itself (single injection);
2) the tell-tale composition can be used in or as a carrier agent in a vaccine;
3) the tell-tale composition can be added in small amounts to a vaccine thereby converting it to a marker vaccine;
4) the tell-tale composition can be used in combination with a pour on medicament;
5) the tell-tale composition can be used as an added ingredient in a topdress product (dry product).

Accordingly, it is an objective of the instant invention to provide a tell-tale composition comprising one or more biodegradable tell-tale materials, in combination with a chemical agent, e.g. a medicament, thereby providing a biodegradable marker.

It is a further objective of the instant invention to teach a method wherein the tell-tale composition is utilized In the food and health industry, such that inspectors in the meat processing industries are provided with a tool for ascertaining the safety of any harvestable animal for inclusion within the human food chain.

DETAILED DESCRIPTION OF THE INVENTION

Now with reference to the instillation/application of medicaments, inclusion of a marker as taught by the instant invention will provide the harvester (packer) with a tool for identifying any animals that pass through their plants. The instant invention particularly sets forth a tell-tale or marking composition which includes a plurality of diverse medicaments, vaccines, or the like. Illustrative of those diverse medicaments, vaccines, or the like contemplated by the invention are those incorporated in Tables 1–9, which are appended hereto. In practice, one or more of said medicaments, vaccines or combinations thereof, which are exemplified by, but not limited to materials selected from the group consisting of steroidal anti-inflammatory agents, non-steroidal anti-inflammatory agents, hormones, nutrient supplements, antibiotics, medicated premixes and feeds, mammary gland antibiotics, bovine vaccines, ovine vaccines, porcine vaccines and mixtures thereof, are included in therapeutically effective amounts. This invention has utility in treating both humans or animals. The tell-tale marker composition can be formulated in any color, and can be visible under a variety of lighting conditions, e.g. full-spectrum visible light, infra-red light, ultra-violet light, monochromatic light or the like.

In a particularly preferred embodiment, the tell-tale marker color will appear under the hide, in the mouth or on the surface of the skin and also can be seen on the outer layer of the hide, skin or hair.

The marker formulation can exhibit a particular initial coloration and subsequently transform to another visually distinct coloration. It also can be injected or given orally at a given day and appear at a later date or appear in a few hours depending on the type and the purpose of the vaccine and how the marker and vaccine are designed to interact. The tell-tale is constructed and arranged to disintegrate or wear away after a given period of time has elapsed, again depending on the use of the marker.

As an example of a desired utility, in the case of swine, if a market animal is vaccinated today and it is desired that the animal be harvested in 30 days, then the marker will be designed to disintegrate in 30 days. If the animal were to be harvested prior to the expiration of the 30 day time period, the harvester will then see the marker on the carcass at the injection site and will thus be warned that the animal has been vaccinated within 30 days prior to harvest. Alternatively, absence of a visible marker at the injection site can serve as an indicator that the animal is clear of any remaining drug residue.

This invention provides the manager of an animal processing facility, e.g. a swine or beef processing facility, with a valuable safety and management tool. The visibility of the marker provides an evidentiary tool as to instillation of the medicament, thereby acting as an aid in managing feedlot personnel to insure compliance with regard to initial application. The feedlot manager can visually inspect the animals after the inoculation should have been given and confirm that instructions have been complied with by virtue of the appearance of a visible marker on the surface of the hide. It will be expected that the marker will mark the underside of the hide, the hide itself or the fat at the injection site on a particular vaccinated animal. For convenience, the injection site on an animal should always be on one particular side of the neck or behind the ear area, thus making the marker easily discoverable. If that marker was set to disintegrate after 30 days and the harvester sees no marker then he knows that animal has not been vaccinated in the last 30 days, however if the marker shows up, then it will be apparent to the harvester that a particular animal has been vaccinated with some kind of vaccine in the last 30 days or any given number of days that the marker is set for. If the marker is used in or with an implant in the ear, for example, it can change color to let the producer know that the implant is running out and needs to be replaced.

Now with reference to human use, this marker can be used in many areas of human treatment wherein vaccines or implants are used. The marker can be useful in functioning as a reactor to the presence of a disease or a reminder of an implant that needs to be replaced. It can be used to see how long the body uses the vaccine, so the marker would disintegrate after a given time period.

Example 1

A study was conducted utilizing a marker on fat tissue that was 2.5" thick. A 1"×16 gauge needle was utilized for instillation of the medicament. The test was done with fat tissue maintained at room temperature, e.g. approximately 78 degrees Fahrenheit.

An injection of the marker was made having a volume of about 2 mL. After one hour, the marker was approximately the size of a dime and the marker went more up and down than to the side or it followed the needle path. A second test was conducted with about 10 mL of marking agent. After one hour has elapsed, the marked area was essentially elliptical in shape and approximately 2.5 inches long. Both marks appeared to follow the needle path and were elliptical or egg shaped.

The particular marker composition can be in the form of one or more types of pigment within an acceptable vehicle or carrier which, because of their physical characteristics, can be readily eliminated from the tissue of an animal or human being. It is within the purview of the instant invention to eliminate the pigment(s) passively via absorption or dissolution into the interstitial fluid or alternatively by active degradation driven by interaction with the hosts immune system. By entrapping, encasing, incorporating, complexing, encapsulating, or otherwise associating these pigments (which are otherwise readily eliminated if placed in the tissue themselves) with an acceptable vehicle or carrier, the marker/vehicle complex so produced possesses a visible color, as well as the necessary physical characteristics to remain within the tissue for a particularly defined time period. In order to provide a controlled visual tool for determining residence time, it is contemplated to provide markers which remain in the tissue for a predetermined period of time (such as several hours, or any number of days, for example 10 days, 30 days, 3, 6, or 9 months, 1,2,5 or 10 years, etc.) and then spontaneously disappear.

These "semi-permanent" or "temporary" tell-tale compositions are formulated by a process which may include one or more of the following mechanisms, such as entrapping, encasing, completing, incorporating, or encapsulating the appropriate markers, which markers are readily eliminated from the tissue, into an appropriate vehicle in combination with one or more medicaments, vaccines or the like. The pigments are designed to slowly bioabsorb, bioerode, or biodegrade over a predetermined period of time. For example, as an aid to serving as a reminder device for an implanted birth control device having up to a five year life span, the pigment will begin to disappear during the fourth and fifth years.

When it is desirable for degradation of the tell-tale marker composition to occur within a relatively short period of time, bioabsorbable microcapsules or microflakes may be utilized. In the case of microcapsules, pigment/vehicle complexes comprise a core of pigment surrounded by the pigment vehicle, which is capable of maintaining its structural integrity until a particular threshold percentage of the pigment vehicle is dissolved, bioeroded, or bioabsorbed. At this point, the pigment vehicle no longer provides protection from elimination. The pigment is then released into the tissue, where it is eliminated over a relatively short period of time.

Alternatively, microflakes made of pigment and pigment vehicle, in which the pigment is mixed throughout the microflakes, maintain a relatively consistent pigmented surface area during the process of bioabsorption. Over a predetermined period of time, the visible pigmented surface dissolves.

The pigment vehicle for the pigment or dye comprises any biologically tolerated material that retains the pigment or dye in the tissue, for whatever time or under whatever conditions are desired. In any of these cases, the pigment vehicle carries a colored pigment or dye suitable for administration into the dermis, or subcutaneous tissue, e.g., the fatty layer underlying the dermis. The pigment vehicle is sufficiently transparent or translucent so as to permit the color of the pigment or dye to show through and be visible. Preferably, the pigment or dye comprises particles smaller than 1 micron. For producing semi-permanent tell-tales, the pigments or dyes are entrapped, encased, complexed, incorporated, encapsulated, or otherwise associated in or with pigment vehicles composed of bioabsorbable, bioerodable, or biodegradable material. The material is designed to bioabsorb, bioerode, or biodegrade over a predetermined period of time so that the pigmented material, when administered into the tissue, creates a marker which lasts only until the pigment vehicle bioabsorbs. Upon partial or complete bioabsorption of the pigment vehicle, the pigment or dye is released, allowing its elimination from the tissue.

A great many biodegradable polymers exist, and the length of time which the pigment lasts in a visible state in the tissue is determined by controlling the type of material and composition of the pigment vehicle. Among the bioabsorbable, bioerodable, or biodegradable polymers which can be used are those disclosed in Higuchi et al., U.S. Pat. Nos. 3,981,303, 3,986,510, and 3,995,635, including zinc alginate poly(lactic acid), poly(vinyl alcohol), polyanhydrides, and poly(glycolic acid). Alternatively, microporous polymers are suitable, including those disclosed in Wong, U.S. Pat. No. 4,853,224, such as polyesters and polyethers, and Kaufman, U.S. Pat. Nos. 4,765,846 and 4,882,150.

Other polymers which degrade slowly in vivo are disclosed in Davis et al., U.S. Pat. No. 5,384,333, which are biodegradable polymers which are solid at 20–37° C. and are flowable, e.g., a liquid, in the temperature range of 38–52° C. Preparation of the tell-tale entails incorporation of the dye or pigment in the polymer matrix, subsequent to which the system may be warmed to approximately 50° C., where it liquifies. The tell-tale composition may then be injected into the tissue, where it cools and resolidifies.

For this type of semi-permanent pigment vehicle, any biodegradable polymer system which has the following characteristics can be used, including homopolymers, copolymers, block copolymers, waxes and gels, as well as mixtures thereof. A preferred polymer system is a triblock copolymer of the general formula A-B-A where A represents a hydrophobic polymer block, and B represents a hydrophilic polymer. The monomers and polymers are preferably linked through ester groups. Preferred hydrophobic polymers and oligomers include, but are not limited to, units selected from polyglycolic acid, polyethylene terephthalate, polybutyl lactone, polycaprolactone, D-polylactic acid, polytetrafluoroethylene, polyolefins, polyethylene oxide, polylactic acid, polyglutamic acid, poly-L-lysine, and poly-L-aspartic acid. Preferred hydrophilic polymers include polyethylene glycol, polypropylene glycol, and poly(vinyl alcohol).

Hydrogel matrices or pigment vehicles for preparing semi-permanent tell-tale markers may be formed by crosslinking a polysaccharide or a mucopolysaccharide with a protein and loading the dye or pigment into the hydrogel matrices. Proteins include both full-length proteins and polypeptide fragments, which in either case may be native, recombinantly produced, or chemically synthesized. Polysaccharides include both polysaccharides and mucopolysaccharides.

A hydrogel in which the tell-tale pigment or dye can be incorporated to a suitable carrier is disclosed in Feijen, U.S. Pat. No. 5,041,292. This hydrogel comprises a protein, a polysaccharide, and a cross-linking agent providing network linkages therebetween wherein the weight ratio of polysaccharide to protein in the matrix is in the range of about 10:90 to about 90:10. The pigment or dye is mixed into this matrix in an amount sufficient to provide color when the hydrogel matrix is administered to the tissue. Examples of suitable polysaccharides include heparin, fractionated heparins, heparan, heparan sulfate, chondroitin sulfate, and dextran, including compounds described in U.S. Pat. No. 4,060,081 to Yannas et al. Using heparin or heparin analogs is preferred because there appears to be reduced immunogenicity. The protein component of the hydrogel may be either a full-length protein or a polypeptide fragment. The protein may be in native form, recombinantly produced, or chemically synthesized. The protein composition may also be a mixture of full-length proteins and/or fragments.

Typically, the protein is selected from the group consisting of albumin, casein, fibrinogen, gamma-globulin, hemoglobin, ferritin and elastin. The protein component may also be a synthetic polypeptide, such as poly-alpha-amino acid. polyaspartic acid or polyglutamic acid. Albumin is the preferred protein component of the matrix, as it is an endogenous material which is biodegradable in blood and tissue by proteolytic enzymes. Furthermore, albumin prevents adhesion of thrombocytes and is nontoxic and non-pyrogenic.

In forming hydrogels containing pigments or dyes; the polysaccharide or mucopolysaccharide and the protein are dissolved in an aqueous medium, followed by addition of an amide bond-forming cross-linking agent. A preferred cross-linking agent for this process is a carbodiimide, preferably the water-soluble diimide N-(3-dimethyl-aminopropyl)-N-ethylcarbodiimide. In this method, the cross-linking agent is added to an aqueous solution of the polysaccharide and protein at an acidic pH and a temperature of about 0 to 50° C., preferably from about 4 to about 37° C., and allowed to react for up to about 48 hours. The hydrogel so formed is then isolated, typically by centrifugation, and washed with a suitable solvent to remove uncoupled material.

Alternatively, a mixture of the selected polysaccharide or mucopolysaccharide and protein is treated with a cross-linking agent having at least two aldehyde groups to form Schiff-base bonds between the components. These bonds are then reduced with an appropriate reducing agent to give stable carbon-nitrogen bonds.

Once the hydrogel is formed, it is loaded with the pigment or dye by immersing the hydrogel in a solution or dispersion of the pigments or dye. The solvent is then evaporated. After equilibration, the loaded hydrogels are dried in vacuo under ambient conditions and stored.

Virtually any pigment or dye may be loaded into the hydrogel vehicles, providing that surface considerations, such as surface charge, size, geometry and hydrophilicity, are taken into account. For example, incorporation and release of a high-molecular weight dye will typically require a hydrogel having a generally lower degree of cross-linking. The release of a charged pigment or dye will be strongly influenced by the charge and charge density available in the hydrogel, as well as by the ionic strength of the surrounding media.

The rate of pigment or dye release from the vehicles can also be influenced by post-treatment of the hydrogel formulations. For example, heparin concentration at the hydrogel surface can be increased by reaction of the formulated hydrogels with activated heparin (i.e., heparin reacted with carbonyldiimidazole and saccharine) or with heparin containing one aldehyde group per molecule. A high concentration of heparin at the hydrogel surface will form an extra "barrier" for positively charged dyes or pigments at physiological pH values. Another way of accomplishing the same result is to treat the hydrogels with positively charged macromolecular compounds like protamine sulfate, polylysine, or like polymers. Another way of varying hydrogel permeability is to treat the surfaces with biodegradable block copolymers containing both hydrophilic and hydrophobic blocks. The hydrophilic block can be a positively charged polymer, like polylysine, while the hydrophilic block can be a biodegradable poly(a-amino acid), such as poly(L-alanine), poly(L-leucine), or similar polymers.

Another slow-release system useful as a marker pigment vehicle for pigments or dyes to form a semi-permanent tell-tale is a dye or pigment and an enzyme encapsulated within a microcapsule having a core formed of a polymer which is specifically degraded by the enzyme and a rate controlling skin. The integrity of the shell is lost when the core is degraded, causing a sudden release of pigment or dye from the capsule. In this type of system, the microcapsule consists of a core made up of a polymer around which there is an ionically-bound skin or shell. The integrity of the skin or shell depends on the structure of the core. An enzyme is encapsulated with the biologically-active substance to be released during manufacture of the core of the microcapsule. The enzyme is selected to degrade the core to a point at which the core can no longer maintain the integrity of the skin, so that the capsule falls apart. An example of such a system consists of an ionically cross-linked polysaccharide, calcium alginate, which is ionically coated with a polycationic skin of poly-L-lysine. The enzyme used to degrade the calcium-alginate coated with poly-L-lysine microcapsules is an alginase from the bacteria Beneckea pelagio or *Pseudomonas putida*. Enzymes exist that degrade most naturally-occurring polymers. For example, the capsule core may be formed of chitin for degradation with chitinase. Other natural or synthetic polymers may also be used and degraded with the appropriate enzyme, usually a hydrogenase.

A particularly preferred bioabsorbable polymer vehicle is a triblock copolymer of poly caprolactone-polyethylene glycol-poly caprolactone. This polymer contains ester bonds which hydrolyze in a hydrophilic environment. The biodegradable polymer matrix should comprise about 30–99% of the tell-tale carrier.

Several mechanisms are involved in the rate and extent of dye or pigment release. In the case of very high molecular weight pigments, the rate of release is more dependent upon the rate of pigment vehicle bioabsorption. With lower molecular weight pigments, the rate of pigment release is more dominated by diffusion. In either case, depending on the particular pigment vehicle composition selected, ionic exchange can also play a major role in the overall release profile.

All references cited herein are hereby incorporated herein in their entirety.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

TABLE 1

| ANTI-INFLAMMATORY |
|---|
| Steroidal Anti-Inflammatory Agents |
| Betamethasone |
| Dexamethasone |
| Flumethasone |
| Methylprednisolone |
| Prednisolone |
| Hydrocortisone |
| Triamcinolone |
| Isoflupredone |
| Prednisolone, Pheniramine and Vitamins |
| Prednisolone, Chlorpheniramine |
| Prednisolone, Trimeprazine |
| Non-Steroidal Anti-Inflammatory Agents |
| Phenylbutazone |
| Dipyrone |
| Flunixine |
| Ketoprofene |
| Orgotein |
| Tolfenamiuc Acid |

TABLE 2

| HORMONES | |
|---|---|
| Anabolic Agents | Other Pituitary or Hypotalamic Hormones |
| Testosterone | |
| Fluoxymesterone | ACTH |
| Boldenone | Osytocine |
| Stanozolol | Cosyntropin |
| Testosterone and | Hyperadrenocorticism Treatment |
| Estradiol | Selegiline |
| Melengestrol | Insulin |
| Gonadotropine Hormones & Releasing Factors | Beef/Pork Insulins<br>Pork Insulin |
| FSH (Folliculo-Stimulating Hormone | Human Biosynthetic Insulin |
| LH (Luteinizing Hormone) | Thyroid Hormones & Anti-Thyroid Products |
| Gonadoreline | Levothyroxine (T-4) |
| PMSG and HCG | Levothyroxine (T-4) |

TABLE 2-continued

HORMONES

| | |
|---|---|
| Mixture | Methinazole |
| Deslorelin | Adrenocortical Hormones |
| Progestagenes | Flurocortisone |
| Progesterone | Desoxycorticosterone |
| Medroxyprogesterone | Hormone Mixtures, Vitamines, |
| Megestrol | Minerals, etc. |
| Altrenogest | Methyltestosterone, |
| Estrogens | Estradiol, Thyroxine, |
| Diethylstilbestrol | Vitamines ADEB |
| Conjugated Estrogens | Antihistamines |
| Luteolytic Products | Dimenhydrinate |
| Dinoprost | Diphenhydramine |
| Cloprostenol | Tripelennamine |
| | Hydroxyzine |
| | Chlorpheniramine |

TABLE 3

NUTRIENT SUPPLEMENTS

VITAMINS ONLY

VITAMIN D
VITAMIN K1
B COMPLEX VITAMINS

TABLE 3-continued

NUTRIENT SUPPLEMENTS

VITAMIN C
COMBINED VITAMINS

COMBINED B COMPLEX
COMBINATIONS OF A AND D
COMBINATIONS OF A, D AND E
VITAMINS AND MINERALS

B COMPLEX VITAMINS WITH
IRON, COPPER AND COBALT
VITAMINS (B COMPLEX) IRON,
COBALT AND CHOLINE
VITAMIN D WITH PHOSPHORUS
VITAMIN E WITH SELENIUM
VITAMINS WITH AMINO-ACIDS

B COMPLEX VITAMINS WITH
AMINO-ACIDS AND CHOLINE
VITAMINS (B COMPLEX),
AMINO-ACIDS, FE, CO, CU
VITAMINS, AMINO-ACIDS,
MINERALS, CLUCIDS

TABLE 4

ANTIBIOTICS

| | | |
|---|---|---|
| NATURAL PENICILLINS | QUINOLONES | COMBINED SULFONAMIDES |
| PENICILLIN G POTASSIUM | CIPROFLOXACIN | SULFAMETHAZINE AND |
| PENICILLIN G SODIUM | ORBIFLOXACIN | SULFATHIAZOLE |
| PENICILLIN G PROCAINE | ENROFLOXACIN | QUINOLONES |
| SEMISYNTHETIC | MACROLIDES | CIPROFLOXACIN |
| PENICILLINES | RIFAMPIN | ORBIFLOXACIN |
| PENICILLIN V | ERYTHROMYCIN | ENROFLOXACIN |
| AMPICILLIN | TYLOSIN | MACROLIDES |
| CLOXACILLIN | TIMICOSIN | RIFAMPIN |
| AMOXICILLIN | ERYTHROMYCIN | TYLOSIN |
| TICARCILLIN | LINCOMYCINES | TIMICOSIN |
| CEPHALOSPORI | CLINDAMYCINE | CLINDAMYCINE |
| CEPHALOTHIN | LINCOMYCINE | LINCOMYCINES |
| CEFAZOLIN | ANTIFUNGAL | CLINDAMYCINE |
| CEFTIOFURE | NYSTATIN | LINCOMYCINE |
| AMINOCYCLITOLS | GRISEOFULVIN | ANTIFUNGAL |
| STREPTOMYCINE | KETOCONAZOLE | NYSTATIN |
| GENTAMYCINE | SULFONAMIDES | GRISEOFULVIN |
| SPECTINOMYCINE | SULFADIMETHOXINE | KETOCONAZOLE |
| TETRACYCLINES | SULFAMETHAZINE | SULFONAMIDES |
| TETRACYCLINES | SALICYLAZOSULFAPYRIDINE | SULFADIMETHOXINE |
| DOXYCYCLINE | SULFAQUINOXALINE | SULFAMETHAZINE |

TABLE 4-continued

ANTIBIOTICS

| | | |
|---|---|---|
| OXYTETRACYCLINE | NITROFURANS | SALICYLAZOSULFAPYRIDINE |
| CHLORAMPHENICOLS | FUMAGILLINE | SULFAQUINOXALINE |
| CHLORAMPHENICOLS | COMBINED PENICILLINES | NITROFURANS |
| FLORFENICOL | PENICILLINE G, PROCAINE AND | FUMAGILLINE |
| QUINOLONES | BENZATHINE | ANTIBIOTICS AND |
| CIPROFLOXACIN | COMBINED SULFONAMIDES | VITAMINS |
| ORBIFLOXACIN | SULFAMETHAZINE AND | PEN-STREP, VITAMINS |
| ENROFLOXACIN | SULFATHIAZOLE | (A, D, E, K, |
| MACROLIDES | SULFONAMIDES COMBINED | B COMPLEX) |
| RIFAMPIN | WITH OTHER ANTIBIOTICS | TRIPLE SULFAS, VITAMINS |
| ERYTHROMYCIN | SULFAQUINOXALINE AND | (AD3, |
| TYLOSIN | PYRIMETHAMINE | B COMPLEX) AND MINERALS |
| TIMICOSIN | SULFADIAZINE AND | NEOMYCINE, |
| LINCOMYCINES | TRIMETHOPRIME | SULFAMETHAZINE, K, |
| CLINDAMYCINE | SULFAMETHOXAZOLE AND | MG, CA, NA, CL, |
| LINCOMYCINE | TRIMETHOPRIME | ACETATE |
| ANTIFUNGAL | SULFADOXINE AND TRIMETHOPRIME | ANTIBIOTICS AND BETA- |
| NYSTATIN | LINCOMYCINE AND | LACTAMASE INHIBITORS |
| GRISEOFULVIN | SPECTINOMYCINE | AMPICILLINE AND |
| KETOCONAZOLE | LINCOMYCINE AND | SULBACTAM |
| SULFONAMIDES | SPECTINOMYCINE | AMOXCILLINE AND |
| SULFADIMETHOXINE | TETRACYCLINES AND | CLAVULINIC ACID |
| SULFAMETHAZINE | NEOMYCINES | TICARCILLIN AND |
| SALICYLAZOSULFAPYRIDINE | TETRACYCLINES AND NEOMYCINE | CLAVULINIC ACID |
| SULFAQUINOXALINE | OXYTETRACYCLINE AND NEOMYCINE | NITROFURANS |
| | ANTIBIOTICS AND ANTI-INFLAMMATORY AGENTS | FUMAGILLINE COMBINED PENICILLINES |
| | TETRACYCLINE, NOVOBIOCINE AND PREDNISOLONE | PENICILLINE G, PROCAINE AND BENZATHINE |

TABLE 5

MEDICATED PREMIXES & FEEDS

ANTIBIOTICS ONLY

TYLOSINE
LINCOMYCINE
PROCAINE PENICILLINE G
TIAMULIN
CHLORTETRACYCLINE
OXYTETRACYCLINE
FLORFENICOL
COMBINED ANTIBIOTICS

LASALOCIDE
AMPROLIUM WITH, OR WITHOUT
ETHOPABATE
DECOQUINATE
MEDICATED FEEDS

LEVAMISOLE
FENBENDAZOLE

TABLE 6

MAMMORY GLAND ANTIBIOTICS

ANTIBIOTICS ONLY

CEPHAPIRINE
ERYTHROMYCINE
CLOXACILLINE
OXYTETRACYCLINE
NOVOBIOCIN
PIRLIMYCINE
COMBINED ANTIBIOTICS

PENICILLINE G, PROCAINE AND
NOVOBIOCINE
PENICILLINE G, PROCAINE AND
DIHYDROSTREPTOMYCINE
PEN G POT, STREPTOMYCINE,
NEOMYCINE AND POLYMYXINE
FOUR ANTIBIOTICS AND
HYDROCORTISONE

TABLE 7

BOVINE VACCINES

BOVINE VACCINES: IBRM-PIM
BOVINE VACCINES: BVDK
BOVINE VACCINES: IBRK-PIK-BVDK
BOVINE VACCINES: IBRM-PIM-BVDM
BOVINE VACCINES: IBRM-BVDM-PIM-CFK-LPK
BOVINE VACCINES: IBEM-PIM-BVDK
BOVINE VACCINES: SVM
BOVINE VACCINES: IBRM-PIM-SVM
INTRAMUSCULAR

BOVINE VACCINES: IBRK-PIK-BVDK-SVK
BOVINE VACCINES: IBRM-PIM-BVDM-SVM
BOVINE VACCINES: IBRM-PIM-BVDK-SVM
BOVINE VACCINES: IBRM-PIM-BVDM-SVK
BOVINE VACCINES: IBRM-PIM-BVDK-SVM
BOVINE VACINES: HSK
BOVINE VACCINES: HSK-PHK BVDM-SVM-HSK
BOVINE VACCINES: IBRM-PIM-BVDK-SVM-LPK
BOVINE VACCINES: IBRK-PIM-BVDK-SVM-LPK
BOVINE VACCINES: IBRK-PIK-BVDK-SVK-LPK
BOVINE VACCINES: IBRM-BVDM-PIM-HSK-LPK-CFK
BOVINE VACCINES: IBRM-PIM-BVDK-SVM-LPK-CFK
BOVINE VACCINES: IBRK-PIK-BVDK-SVK-LPK-HSK
BOVINE VACCINES: RCM
BOVINE VACCINES: CFK
BOVINE VACCINES: CFK-LPK
BOVINE VACCINES: ECK (MASTITIS)
BOVINE VACCINES: SAK
BOVINE VACCINES: PPK
BOVINE VACCINES: BAM
BOVINE VACCINES: TVM
BOVINE VACCINES: MOK
BOVINE VACCINES: 4CLOSTRIDIUM-K - ENTK
BOVINE VACCINES: 4CLOSTRIDIUM-K - ENTK-HSK

TABLE 8

OVINE VACCINES

OVINE VACCINES: ENTK-PSTK-TTK
OVINE VACCINES: ENTK-PSTK-TTK-3 CLOSTRIDIUM-K
OVINE VACCINES: CHK
OVINE VACCINES: CFK-CHK
OVINE VACCINES: ENTK-4CLOSTRIDIUM-K
OVINE VACCINES: ENTK-TTK-3 CLOSTRIDIUM-K
OVINE VACCINES: ENTK-5 CLOSTRIDIUM-K
OVINE VACCINES: FNK

TABLE 9

PORCINE VACCINES

| | |
|---|---|
| PROCINE VACCINES: BOK | RABIES |
| PORCINE VACCINES: BOK-PAK | |
| PORCINE VACCINES: ERK | BOVINE, OVINE |
| PORCINE VACCINES: ERM | |
| PORCINE VACCINES: BOK-PAK-ERK | TETNUS |
| PORCINE VACCINES: ECK | BOVINE, OVINE |
| PORCINE VACCINES: ENTK-ECK | |
| PORCINE VACCINES: BOK-PAK-ECK | LEPTOSPIRA |
| PORCINE VACCINES: LPK | BOVINE AND PORCINE |
| PORCINE VACCINES: BOK-PAK-ERK-ECK | |
| PORCINE VACCINES: PVK | |
| PORCINE VACCINES: ERK-PVK | |
| PORCINE VACCINES: ERK-LPK-PVK | |
| PORCINE VACCINES: TGEM | |
| PORCINE VACCINES: TGEK | |
| PORCINE VACCINES: ROM | |

TABLE 9-continued

PORCINE VACCINES

PORCINE VACCINES: TGEM-ROM
PORCINE VACCINES: TGEK-ROM
PORCINE VACCINES: ECK-TGEM-ROM
PORCINE VACCINES: APK
PORCINE VACCINES: BOK-PAK-ERK-APK
PORCINE VACCINES: ECK-TGEM-ROM-ENTK
PORCINE VACCINES: BOK-PAK-ENTK-ECK-ERK-ROM-TGEM
PORCINE VACCINES: BOK-PAK-MHK
PORCINE VACCINES: STK
PORCINE VACCINES: MHK
PORCINE VACCINES: HPK
PORCINE VACCINES: HPK-MHK
PORCINE VACCINES: ERK-HPK
PORCINE VACCINES: RRSM
PORCINE VACCINES: INK

What is claimed is:

1. A process for visually determining the residence time of a therapeutically effective amount of one or more medicaments, vaccines or combinations thereof comprising:

providing a biodegradable tell-tale composition which is applied cutaneously to a human or animal subject for aiding in the determination of instillation or application of a medicament, vaccine or combinations thereof;

formulating an effective amount of a marker formulation having a pigment or dye in combination with a suitable carrier therefore;

incorporating within said marker formulation a therapeutically effective amount of one or more medicaments, vaccines or combinations thereof;

designing a controllable period of visibility of said marker to provide a controlled visual tool for determining residence time of said therapeutically effective amount of one or more medicaments, vaccines or combinations thereof; and applying or instilling said tell-tale composition to said animal or human.

2. The process of claim 1, wherein:

said one or more medicaments, vaccines or combinations thereof are selected from the group consisting of steroidal anti-inflammatory agents, non-steroidal anti-inflammatory agents, hormones, nutrient supplements, antibiotics, medicated premixes and feeds, mammary gland antibiotics, bovine vaccines, ovine vaccines, porcine vaccines and mixtures thereof.

3. The process of claim 1, wherein:

said marker formulation can be in the form of one or more types of pigment within an acceptable vehicle or carrier which are constructed and arranged to be readily eliminated from the tissue of an animal or human being.

4. The process of claim 1, wherein:

said tell-tale marker formulation can be formulated in any color, and can be visible under a light sources selected from the group consisting of full-spectrum visible light, infra-red light, ultra-violet light, monochromatic light or combinations thereof.

5. The process of claim 1, wherein:

said marker formulation is constructed and arranged to exhibit a particular initial coloration and subsequently transform to another visually distinct coloration.

6. The process of claim 1, wherein:
said marker formulation is manufactured by entrapping, encasing, incorporating, complexing, encapsulating, or otherwise associating said pigment or dye with an acceptable vehicle or carrier composition.

7. The process of claim 1, wherein:
said pigment or dye is constructed and arranged to slowly bioabsorb, bioerode, or biodegrade over a predetermined period of time.

8. The process of claim 7 wherein:
said predetermined period of time is in the range of from several hours up to about 5 years.

9. The process of claim 1 wherein:
the marker formulation is in the form of bioabsorbable microcapsules.

10. The process of claim 1 wherein:
the marker formulation is in the form of microflakes.

11. The process of claim 1 wherein:
said bioabsorbable microcapsules comprise a core of said pigment or dye surrounded by said suitable carrier therefore;
said pigment or dye is constructed and arranged to maintain the structural integrity thereof until a particular threshold percentage of the carrier is dissolved, bioeroded, or bioabsorbed;
wherein said pigment or dye is then released into the tissue, and eliminated therefrom.

12. The process of claim 1 wherein:
said suitable carrier comprises any biologically tolerated material that retains the pigment or dye in the tissue, for a particularly defined time period effective to provide a controlled visual tool for determining residence time of said therapeutically effective amount of one or more medicaments, vaccines or combinations thereof.

13. The process of claim 1 wherein:
said marker formulation includes a suitable carrier in combination with a colored pigment or dye, said colored pigment or dye being suitable for administration into cutaneous or subcutaneous tissue, and wherein said suitable carrier is sufficiently transparent or translucent so as to permit the color of the pigment or dye to show through and be visible.

14. The process of claim 1 wherein:
said suitable carrier is selected from the group consisting of bioabsorbable, bioerodable, and biodegradable polymers.

15. The process of claim 1 wherein:
said suitable carrier is selected from the group consisting of zinc alginate poly(lactic acid), poly(vinyl alcohol), polyanhydrides, poly(glycolic acid) and mixtures thereof.

16. The process of claim 1 wherein:
said suitable carrier is a microporous polymer selected from the group consisting of polyesters and polyethers.

17. The process of claim 1 wherein:
said suitable carrier is a polymer which degrades slowly in vivo selected from the group consisting of biodegradable polymers which are solid at 20–37° C. and are flowable in the temperature range of 38–52° C.

18. The process of claim 1 wherein:
said suitable carrier is a biodegradable polymer system is selected from the group consisting of homopolymers, copolymers, block copolymers, waxes, gels and mixtures thereof.

19. The process of claim 1 wherein:
said suitable carrier is a triblock copolymer of he general formula A-B-A where A represents a hydrophobic polymer block, and B represents a hydrophilic polymer.

20. The process of claim 1 wherein:
said suitable carrier is a group of monomers and polymers linked through ester groups.

21. The process of claim 1 wherein:
said suitable carrier includes hydrophobic polymers and oligomers selected from the group consisting of units selected from polyglycolic acid, polyethylene terephthalate, polybutyl lactone, polycaprolactone, D-polylactic acid, polytetrafluoroethylene, polyolefins, polyethylene oxide, polylactic acid, polyglutamic acid, poly-L-lysine, and poly-L-aspartic acid.

22. The process of claim 1 wherein:
said hydrophilic polymers include one or more polymers selected from the group consisting of polyethylene glycol, polypropylene glycol, and poly(vinyl alcohol).

23. The process of claim 1 wherein:
said suitable carrier is a hydrogel matrix formed by crosslinking a polysaccharide or a mucopolysaccharide with a protein wherein said dye or pigment is loaded within said hydrogel matrix.

24. The process of claim 1 wherein:
said suitable carrier is in the form of an enzyme encapsulated within a microcapsule having a core formed of a polymer which is specifically degraded by the enzyme and a rate controlling skin;
wherein as the integrity of the skin is lost during degradation of said core, pigment or dye is released.

* * * * *